(12) United States Patent
Boyd et al.

(10) Patent No.: US 10,458,634 B2
(45) Date of Patent: Oct. 29, 2019

(54) ADJUSTABLE SURGICAL LIGHT DEVICE AND SYSTEM

(71) Applicant: Palmetto Biomedical Inc., Durham, NC (US)

(72) Inventors: Lawrence M. Boyd, Durham, NC (US); John J. Ratcliffe, Raleigh, NC (US)

(73) Assignee: Palmetto Biomedical Inc., Durham, NC (US)

( * ) Notice: Subject to any disclaimer, the term of this patent is extended or adjusted under 35 U.S.C. 154(b) by 20 days.

(21) Appl. No.: 15/862,747

(22) Filed: Jan. 5, 2018

(65) Prior Publication Data

US 2018/0128463 A1    May 10, 2018

Related U.S. Application Data

(63) Continuation of application No. 14/177,887, filed on Feb. 11, 2014, now abandoned.
(Continued)

(51) Int. Cl.
*F21V 21/32* (2006.01)
*F21L 4/04* (2006.01)
(Continued)

(52) U.S. Cl.
CPC .............. *F21V 21/32* (2013.01); *A61B 46/10* (2016.02); *A61B 90/30* (2016.02); *F21L 4/04* (2013.01); *F21V 21/08* (2013.01); *F21V 23/06* (2013.01); *A61B 2017/00734* (2013.01); *A61B 2090/306* (2016.02); *A61B 2090/308* (2016.02); *F21W 2131/20* (2013.01)

(58) Field of Classification Search
CPC .......... F21V 21/32; F21V 21/08; F21V 23/06; F21V 23/023; F21W 2131/20; A61B 90/30; A61B 90/35; A61B 2090/308; A61B 2090/306; A61B 2090/309; A61B 2017/00734; A61B 46/10; F21L 4/04
See application file for complete search history.

(56) References Cited

U.S. PATENT DOCUMENTS 4,797,798 A * 1/1989 Schumaker ............. F21S 6/006
                                                              248/161
4,843,530 A * 6/1989 Mori ....................... A61N 5/06
                                                              362/413
(Continued)

FOREIGN PATENT DOCUMENTS

WO     WO2011103073      *   8/2011

*Primary Examiner* — Erin Kryukova
(74) *Attorney, Agent, or Firm* — Maginot, Moore & Beck, LLP

(57) ABSTRACT

An adjustable light for a medical environment comprises a first housing adapted for engagement with a handle of an overhead light, a second housing including a lamp operatively connected to a power source for generating illuminating light, and a flexible shaft extending between and interconnecting the first housing at a proximal end of the shaft and the second housing at a distal end of the shaft. The first housing is adapted to be releasably coupled to the handle of the overhead light over a work area such that the flexible arm and the second housing are selectively movable relative to the first housing toward a target in the work area for illuminating the target.

16 Claims, 13 Drawing Sheets

Related U.S. Application Data

(60) Provisional application No. 61/763,175, filed on Feb. 11, 2013.

(51) Int. Cl.
*F21V 21/08* (2006.01)
*F21V 23/06* (2006.01)
*A61B 90/30* (2016.01)
*A61B 46/10* (2016.01)
*F21W 131/20* (2006.01)
*A61B 17/00* (2006.01)

(56) References Cited

U.S. PATENT DOCUMENTS

| | | | | |
|---|---|---|---|---|
| 5,707,137 A * | 1/1998 | Hon | ............ | F21L 4/04 362/183 |
| 6,257,745 B1 * | 7/2001 | Speth | ............ | F21V 21/32 362/197 |
| 6,464,383 B1 * | 10/2002 | Northington | ............ | A61B 90/35 362/572 |
| 6,601,985 B1 * | 8/2003 | Jesurun | ............ | F21S 2/00 362/552 |
| 8,317,371 B1 * | 11/2012 | Khosrow | ............ | F21S 8/03 362/184 |
| 2003/0016532 A1 * | 1/2003 | Reed | ............ | F21S 9/02 362/198 |
| 2004/0141317 A1 * | 7/2004 | Sun | ............ | F21L 4/06 362/198 |
| 2004/0264193 A1 * | 12/2004 | Okumura | ............ | F21S 10/02 362/276 |
| 2005/0171407 A1 * | 8/2005 | Rosenkranz | ............ | F21S 9/02 600/249 |
| 2005/0242261 A1 * | 11/2005 | Brahler | ............ | E04B 9/006 248/326 |
| 2006/0082993 A1 * | 4/2006 | Hsu | ............ | F21S 9/02 362/197 |
| 2006/0127167 A1 * | 6/2006 | Hsieh | ............ | F16B 2/185 403/109.5 |
| 2007/0058365 A1 * | 3/2007 | Anderson | ............ | F21L 4/04 362/198 |
| 2009/0086495 A1 * | 4/2009 | Chen | ............ | A61B 90/35 362/427 |
| 2009/0316437 A1 * | 12/2009 | Gibbons | ............ | F21S 6/003 362/647 |
| 2011/0013383 A1 * | 1/2011 | Medinis | ............ | F21V 21/084 362/105 |
| 2011/0135295 A1 * | 6/2011 | Gharibian | ............ | A61B 1/00128 396/448 |
| 2013/0069549 A1 * | 3/2013 | Kreitzer | ............ | F21S 6/003 315/200 R |

\* cited by examiner

ADJUSTABLE SURGICAL LIGHT DEVICE AND SYSTEM

CROSS REFERENCE TO RELATED APPLICATIONS

This application is a continuation of and claims priority to co-pending application Ser. No. 14/177,887, filed on Feb. 11, 2014, which claims priority to related to U.S. provisional application No. 61/763,175, filed Feb. 11, 2013, entitled "TARGETED AND ADJUSTABLE SURGICAL LIGHTING SYSTEM", naming Lawrence M. Boyd and John J. Ratcliffe as the inventors. The contents of the provisional application are incorporated herein by reference in their entirety.

BACKGROUND

A device is described that relates generally to lighting used in the performance of a surgical or other medical procedure and, more particularly, to an adjustable light device that may be detachably connected to an overhead light whereby the light may be brought in close proximity with objects to be illuminated.

Surgical lighting generally includes overhead lighting, head lamps worn by the surgeons and lighted instruments placed within a wound. Sufficient lighting of the tissues is critical in surgery so that the surgeon can accurately identify the tissues in order to make sure that the appropriate tissues are targeted while avoiding damage to surrounding vascular and neural structures. For example, in a minimally invasive spinal fusion, the surgeon will need to identify bony structures, remove degenerated intervertebral disc tissues and avoid any damage to the spinal cord, peripheral nerves and vascular structures. In addition, should a structure be unintentionally damaged, powerful and targeted lighting may be needed to allow for rapid and complete surgical repair.

Current surgical lighting is not optimal for many surgical procedures, especially for those utilizing minimal incisions and deep access corridors into the body. The majority of surgical lighting is wired to A.C. current in the operating room, creating a possibility of electrical shock and also requiring wiring on the floor of the operating room, which is a tripping hazard. These are typically costly and permanent lighting systems.

Overhead lights are large and expensive dual (or more) lighting systems affixed to the ceiling of the operating room. The overhead lighting systems broadly direct light downward onto the patient and surgical field. Generally cylindrical handles on the overhead lights may be used by the surgeons to manually adjust the direction of the light. Sterile coverings are used for the light handles. In some cases, a sterile light handle cover may be threaded onto the handle. In other cases, the handle cover may be a thin, flexible plastic piece adapted to slip over the handle. In general, overhead surgical lighting systems provide good lighting of the surgical field and patient surface, but provide less direct and targeted lighting down into the body cavity. This is especially true for small incision situations seen in minimally invasive surgery. However, because the light source is above the surgeon's head, leaning in toward the surgical site may obscure the light source and create shadows.

Surgeons may wear fiber optic lighting systems anchored to their foreheads with a targeted beam shining downward. The light beam may be adjusted to focus directly downward along the path of the surgeon's view. These systems can provide targeted light into smaller incisions. However, these systems commonly become less targeted over the course of a surgical procedure and need to be re-adjusted by the non-sterile nursing staff since they are not sterile systems. When head lamps are worn by multiple surgeons in the same procedure, the two head lamps may bump into one another. In addition, these systems typically require anchorage to a light source and a power source resting on a stand behind the operating surgeon. This can limit the surgeon's mobility, as well as creating a tripping hazard in the operating room. Some such systems may be battery powered, but then require the surgeon to wear a heavy rechargeable battery pack around their waist. Finally, the lighting harness secured to the surgeon's forehead can create neck strain over the course of a long surgical procedure.

Surgical instruments placed down into the wound may be provided with illumination sources. In one example, this involves the addition of lighting cables to surgical retractors. While this solution does provide for more directed lighting in the work space, the light cables add expense, take up working space and may require enlarging the incision, and can generate heat. Cases of skin burns or even burning or melting of draping have been reported. A handheld and separate light source, such as a surgical wand or probe, may also be used, but this still requires a cable for lighting with coincident issues of heating and impeding of the operative field.

For the foregoing reasons, there is a need for an improved adjustable light device that may be used in a surgical or other medical environment. The light device should be adjustable for selectively targeting the light to a preferred location. Ideally, the new light device will work in conjunction with available lighting systems.

SUMMARY

An adjustable light is provided for use in a medical environment including an overhead light having a light handle. The adjustable light comprises a first housing adapted for engagement with the handle of the overhead light, a second housing including a lamp operatively connected to a power source for generating illuminating light, and a flexible shaft extending between and interconnecting the first housing at a proximal end of the shaft and the second housing at a distal end of the shaft. The first housing is adapted to be releasably coupled to the handle of the overhead light over a work area such that the flexible arm and the second housing are selectively movable relative to the first housing toward a target in the work area for illuminating the target.

A lighting system is also provided for a medical environment including a ceiling. The lighting system comprises an overhead light adapted to be suspended from the ceiling, the overhead light including a handle, a first housing configured for engagement with the handle of the overhead light, a second housing including a lamp operatively connected to a power source for generating illuminating light, and a flexible shaft extending between and interconnecting the first housing at a proximal end of the shaft and the second housing at a distal end of the shaft. The first housing is releasably coupled to the overhead light over a work area such that the flexible arm and the second housing are selectively movable relative to the first housing toward a target in the work area for illuminating the target.

DETAILED DESCRIPTION

Figure 1:
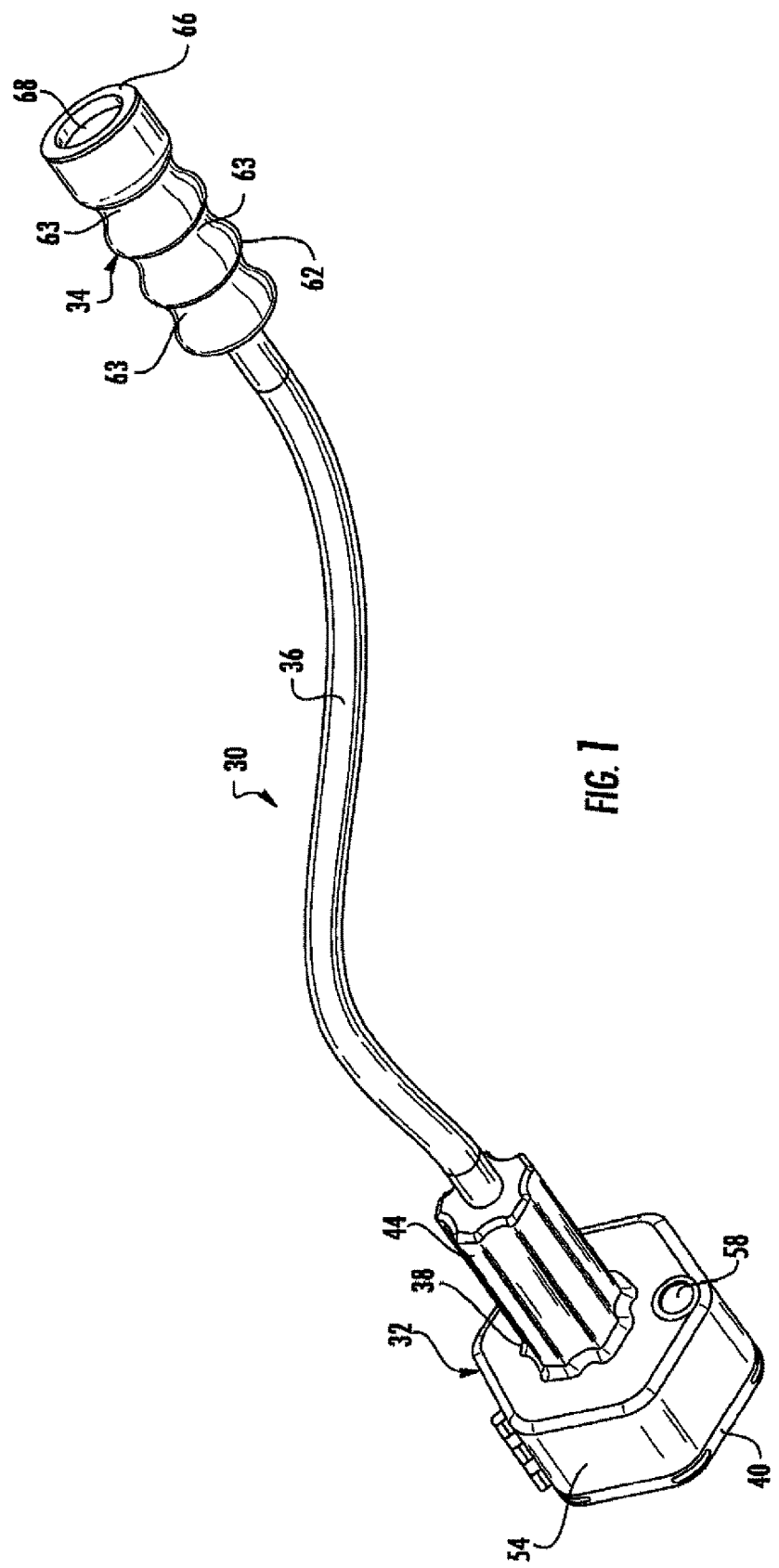
FIG. 1 is a side perspective view of an embodiment of a flexible and adjustable surgical light configured for attachment to an overhead light.

For the purposes of promoting an understanding of the principles of the surgical light device and system, reference will now be made to the embodiments illustrated in the drawings and described in the following written specification. It is understood that no limitation to the scope of the surgical light device and system is thereby intended. It is further understood that the present surgical light device and system includes any alterations and modifications to the illustrated embodiments and includes further applications of the principles of the surgical light device and system as would normally occur to one skilled in the art to which this surgical lighting system pertains.

In one embodiment, the surgical light device and system described herein contemplates a device and a procedure that is implemented in the setting of a surgical environment for providing lighting into the surgical working space created by an incision. Access to the internal working space may be secured by a trocar, tube or bladed retractors, for example. In all cases, lighting of the internal cavity is required for a safe and accurate surgical procedure. Lighting of the surgical working space may be especially challenging in so-called "minimally invasive" or "minimal incision" procedures where the amount of tissue incised is minimized and, therefore, a small opening is available for directing light into the body.

Figure 2:
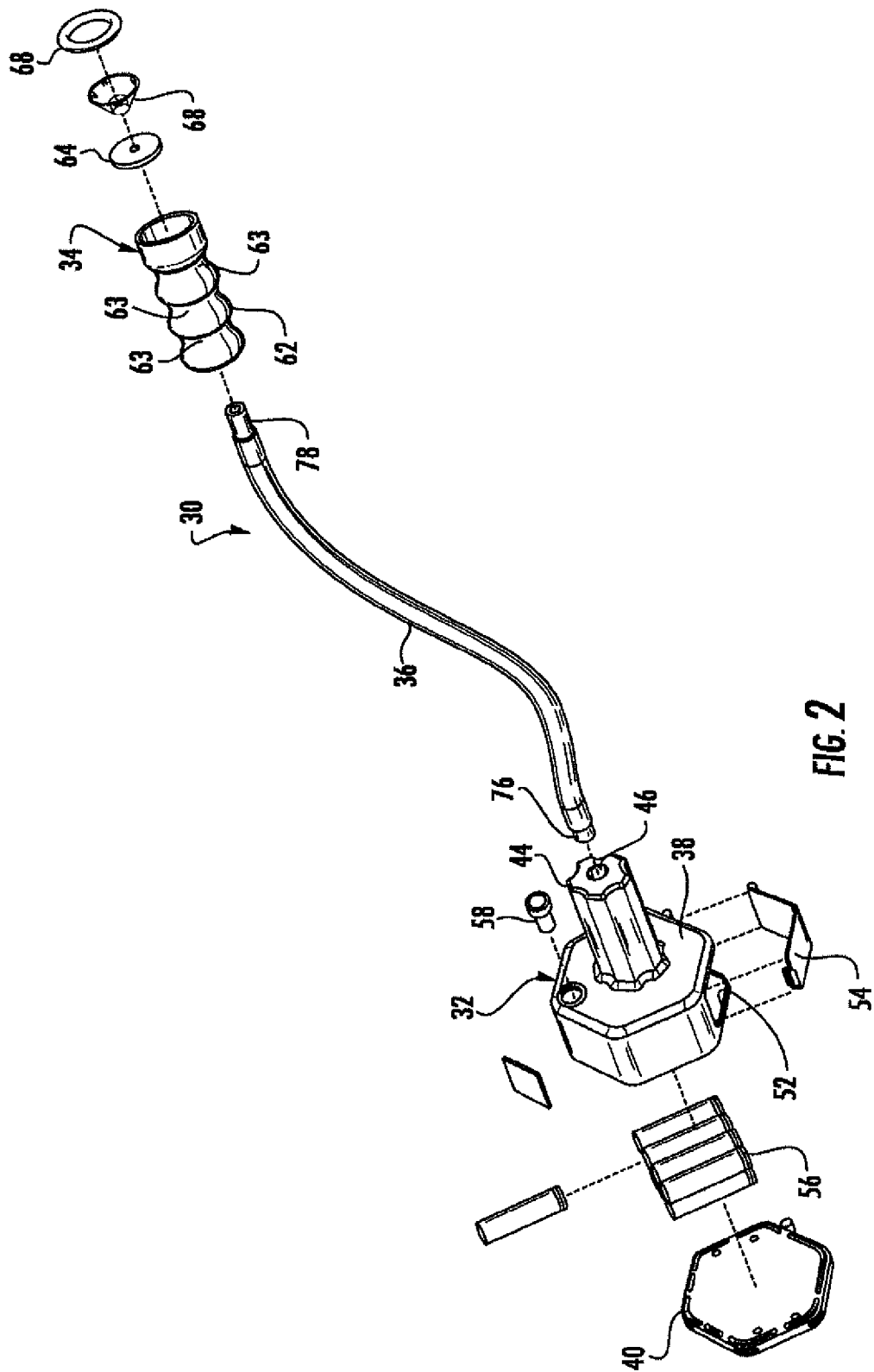
FIG. 2 is an exploded perspective view of the embodiment of the surgical light as shown in FIG. 1.
Figure 3:
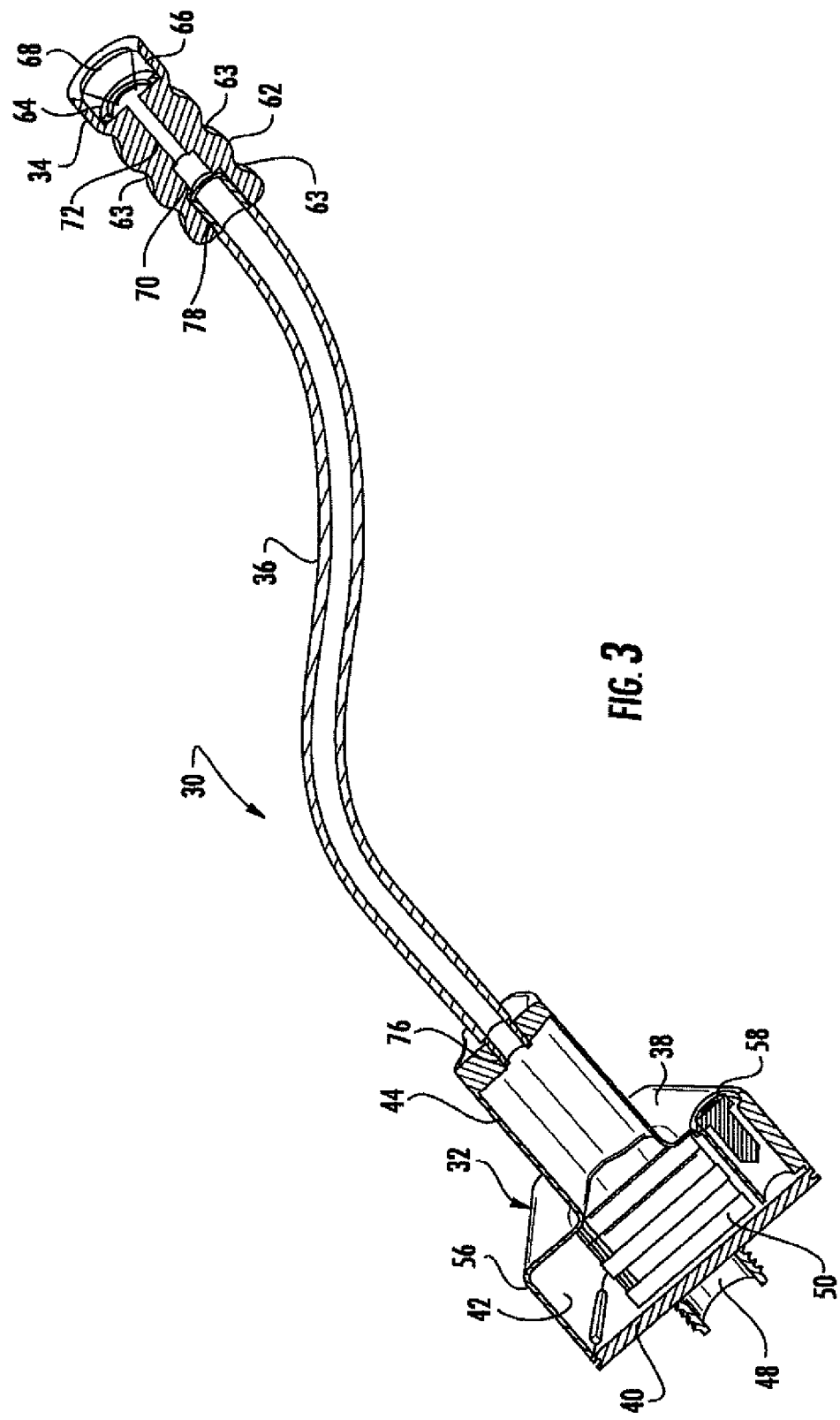
FIG. 3 is a longitudinal cross-section view of the embodiment of the surgical light as shown in FIG. 1.
Figure 4:
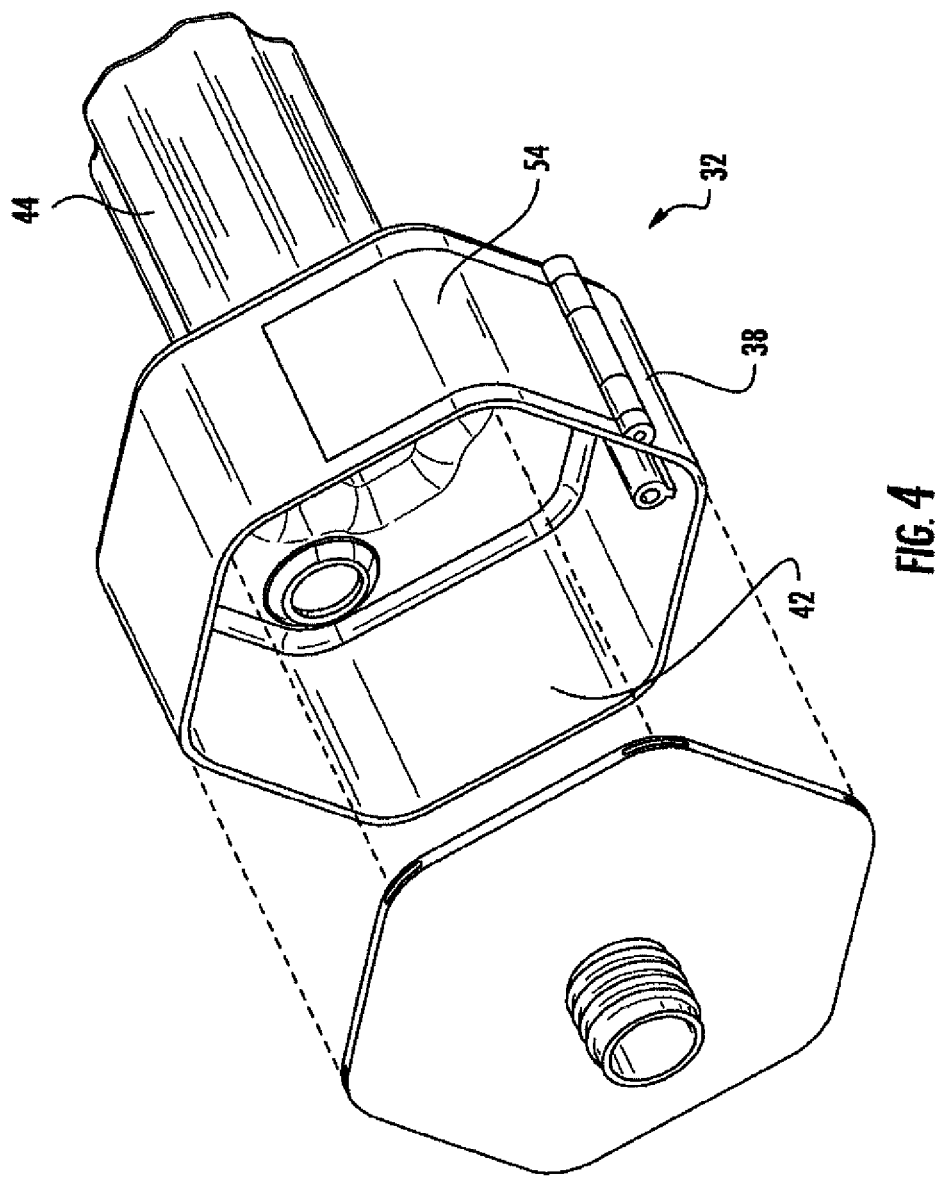
FIG. 4 is a rear exploded perspective view of an embodiment of a base housing for use with the surgical light as shown in FIG. 1.
Figure 5:
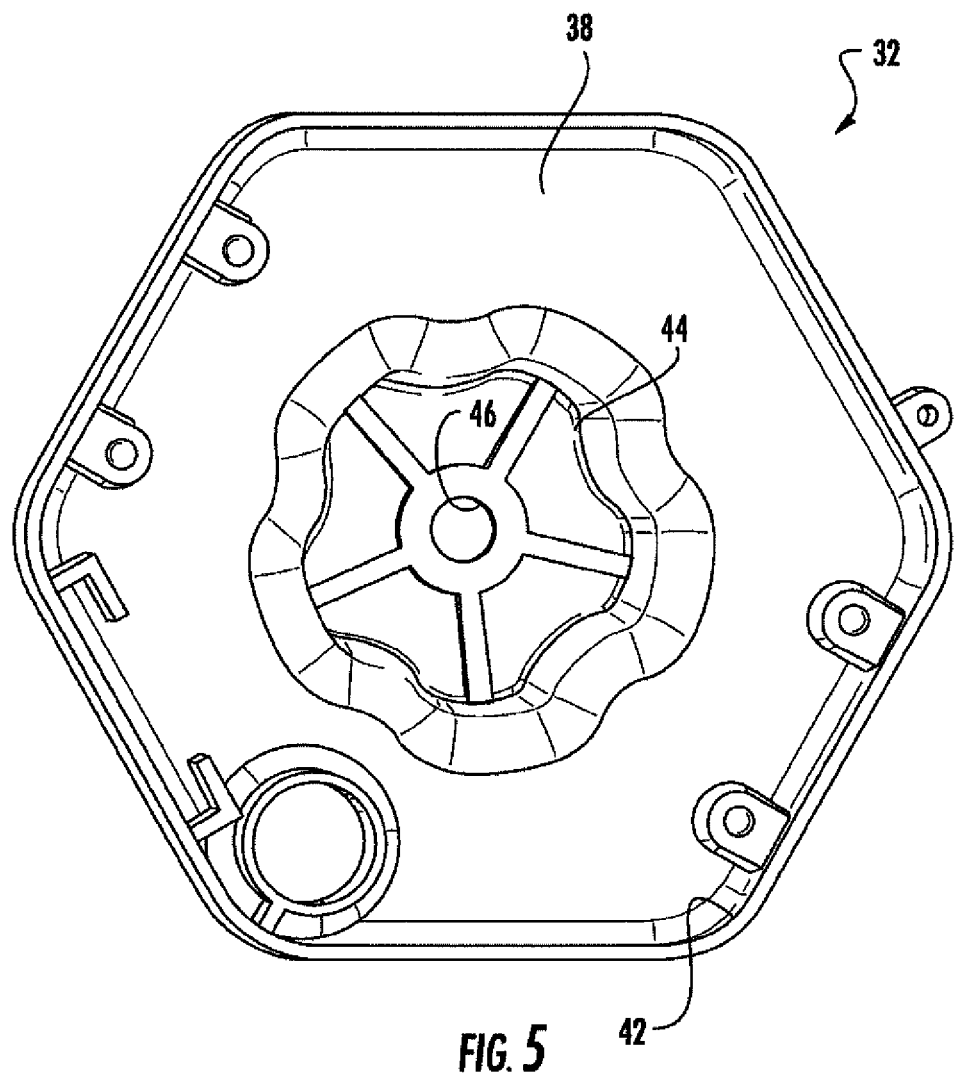
FIG. 5 is a rear plan view of the embodiment of the base housing as shown in FIG. 4.

An embodiment of a surgical light device is shown in FIGS. 1-3 and generally designated at 30. The surgical lighting device 30 comprises a proximal anchor member 32 fabricated, for example, of a medical grade polymer and a distal light assembly 34. An intermediate flexible shaft 36 extends between and interconnects the anchor member 32 and the light assembly 34. The flexible shaft 36 enables the light assembly 34 to be moved independently of the anchor member 32. Referring to FIGS. 4 and 5, one embodiment of the anchor member 32 comprises a housing 38 and a removable proximal cover 40. The housing 38 defines an interior cavity 42. A hollow central axial projection 44 extends distally from the housing 38. The distal end of the projection 44 has a hole 46 opening into the interior of the projection 44 and the cavity 42 of the housing 38. The cover 40 has a central axial threaded flange 48 extending proximally from the housing 38. In this embodiment, the threaded flange 48 is used to threadably connect the anchor member 32 to an overhead light, which will be described below.

The housing 38 may be configured to accommodate batteries 50 for providing a power to the light assembly 34 in a conventional manner. The housing 38 is provided with a peripheral opening 52 for accessing the batteries for insertion or replacement. The opening 52 is selectively accessed via a panel 54 which is mounted on a hinge 55 to the housing 38. An integrated battery case 56 may be provided for holding the batteries 50. Alternatively, a rechargeable battery pack (not shown) or a battery pack having a power cord (not shown) may be used to power the light assembly 34. An adaptor connection may be provided in the housing 38 for recharging. Preferably, the batteries 50 are configured to provide sufficient power for about 6 to about 8 hours of light. The batteries 50 can be replaced after a fixed period for very long usage times during, for example, lengthy surgical procedures. In another embodiment, the anchor member 32 may be connected to a source of A.C. electrical power via a conventional power cord (not shown) as a means for conveying power from the power source.

In the embodiment shown, the housing 38 is generally hexagonal in transverse cross-section. It is understood that this is merely exemplary and that the housing 38 may be configured in any number of convenient shapes, including cylindrical, cubic or even irregular. Moreover, the size of the housing 38 may vary to accommodate the internal components, including the batteries, or to correspond to the configuration of an overhead light for attachment to the overhead light. For example, a relatively large housing 38 may be used to accommodate more batteries 50 and increase the illumination output. Accordingly, the surgical light device 30 is adaptable to various applications and environments.

An on-off switch 58 is provided on the housing 48 of the anchor member 32 for allowing the user to selectively actuate the light assembly 34. The switch 58 can be closed by means of a push button 60 which completes a circuit between the batteries 50, or other power source, and the light assembly 34 in a conventional manner.

The light assembly 34 comprises a generally cylindrical head portion 62, a PC board 64 including a driver and an LED light source, a lens 66, and a retaining ring 68. The head portion 62 is preferably formed from anodized aluminum and serves as a heat sink for dissipating the heat of the LED. The head portion 62 defines a central axial through bore of varying diameter. The head portion 62 defining the bore at the proximal end 70 is threaded and is sized to receive the distal end of the flexible shaft 36. The intermediate portion of the bore 72 has a much smaller diameter and is sized sufficiently for passing electrical wiring to the PC board. The bore at the distal end 74 of the head portion 62 is configured to receive the PC board 64, the lens 66 and the retaining ring 68. The lens 66 is bell-shaped and defines an opening at a small end thereof through which the LED extends. The retaining ring 68 overlies the periphery of the front surface of the lens 66. The change in diameter of the bore from the intermediate portion 72 of the bore to the distal end 74 of the head portion 62 forms a seat in the head portion for supporting the PC board 64. The retaining ring 68 is secured in place with adhesive for securing the components in the distal end 74 of the head portion 62. The periphery of the head portion 62 has a plurality of axially-spaced circumferential grooves 63 to aid in the handling of the head portion.

The LED light source of the light assembly 34 generates substantial light without appreciable heat generation. A variety of light emitting diodes in a variety of colors may be used. The use of different colors may provide for reduced eye strain for the surgical team or may help to better identify and differentiate different types of tissues at the surgical site. Additionally, multiple lights may be used during the procedure, either attached at a common anchor point or attached to separate surgical lights. The use of various intensity and wavelength lights is also contemplated, allowing the surgical team to select the appropriate light at the time of surgery. Lights allowing for use of fluorescent tracers in the operative space may be useful in targeting, for example, tumors of the cranial space or breast tissue. As an alternative to an LED light source, other suitable light sources may be used, including a conventional halogen bulb with an integral reflector. Ultraviolet (UV) irradiation could also be delivered at the distal end of the shaft 36 to provide for localized killing of pathogenic agents on the skin or at the operative site. For UV applications, a mercury high pressure lamp, a metal vapor or xenon high pressure lamp or super pressure lamps, or a tungsten filament incandescent lamp are suitable.

The flexible shaft 36 comprises a hollow tubular element formed from a flexible material, such as a plastic or metal. For example, a suitable flexible framework may be constructed from a thin-walled corrugated metal tube; however, it is understood that the flexible framework may comprise other components, such as interconnected circular rings or wire portions, alternating metal and composite members, universally rotatable or pivotable members, and the like. The flexible shaft 36 permits manual deformation for adjusting the position of the light assembly 34, which remains fixed indefinitely until readjusted by the user. A suitable flexible shaft is sold as a flex arm available from Moffatt Products Inc. of Watertown, S. Dak.

Each of the ends of the shaft 36 includes an externally threaded fitting 76. The distal end of the projection 44 on the housing 48 of the anchor member 32 is internally threaded for threadingly engaging the fitting 76 at the proximal end of the shaft 36. Similarly, the proximal end of the head portion 62 of the light assembly 34 is internally threaded for threadingly engaging the distal end 78 of the shaft 36. The length of the shaft 36 may vary to suit the environment such as, for example, a particular operative suite. In an alternative embodiment, the flexible shaft 34 may comprise a retractable mechanism for deploying only a length of shaft 36 necessary for a particular application. In the embodiment shown, the diameter flexible shaft 36 is essentially identical along its length between the proximal end 76 and the distal end 78 of the shaft.

Electrical wiring, not shown for clarity, extends axially through the shaft 36 between the batteries 50, or other power source, in the anchor member 32 to the light assembly 34. The electrical power is transmitted via the wiring from the anchor member 32 and along the shaft 36 to the light assembly 34 for illuminating an area for medical treatment purposes. In addition, some embodiments may need to anticipate the need for nested wiring corridors such as those incorporated into the surgical lighting system 30. Such a design anticipates a high volume and disposable device that may be useful in large scale applications in hospitals, surgical centers and outpatient clinics and physician offices.

Figure 6:
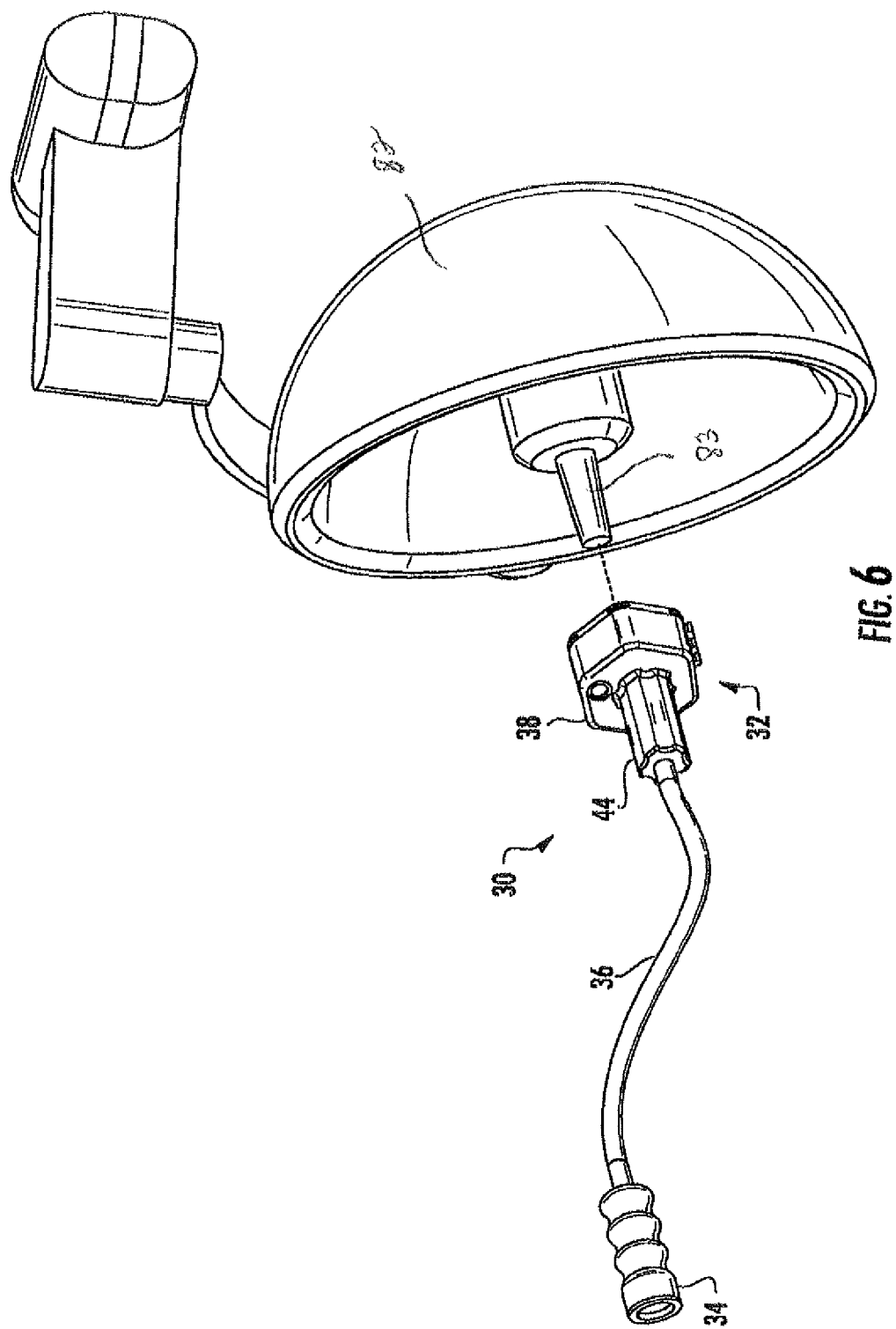
FIG. 6 is a front exploded perspective view of the embodiment of the surgical light as shown in FIG. 1 and an overhead surgical light.
Figure 7:
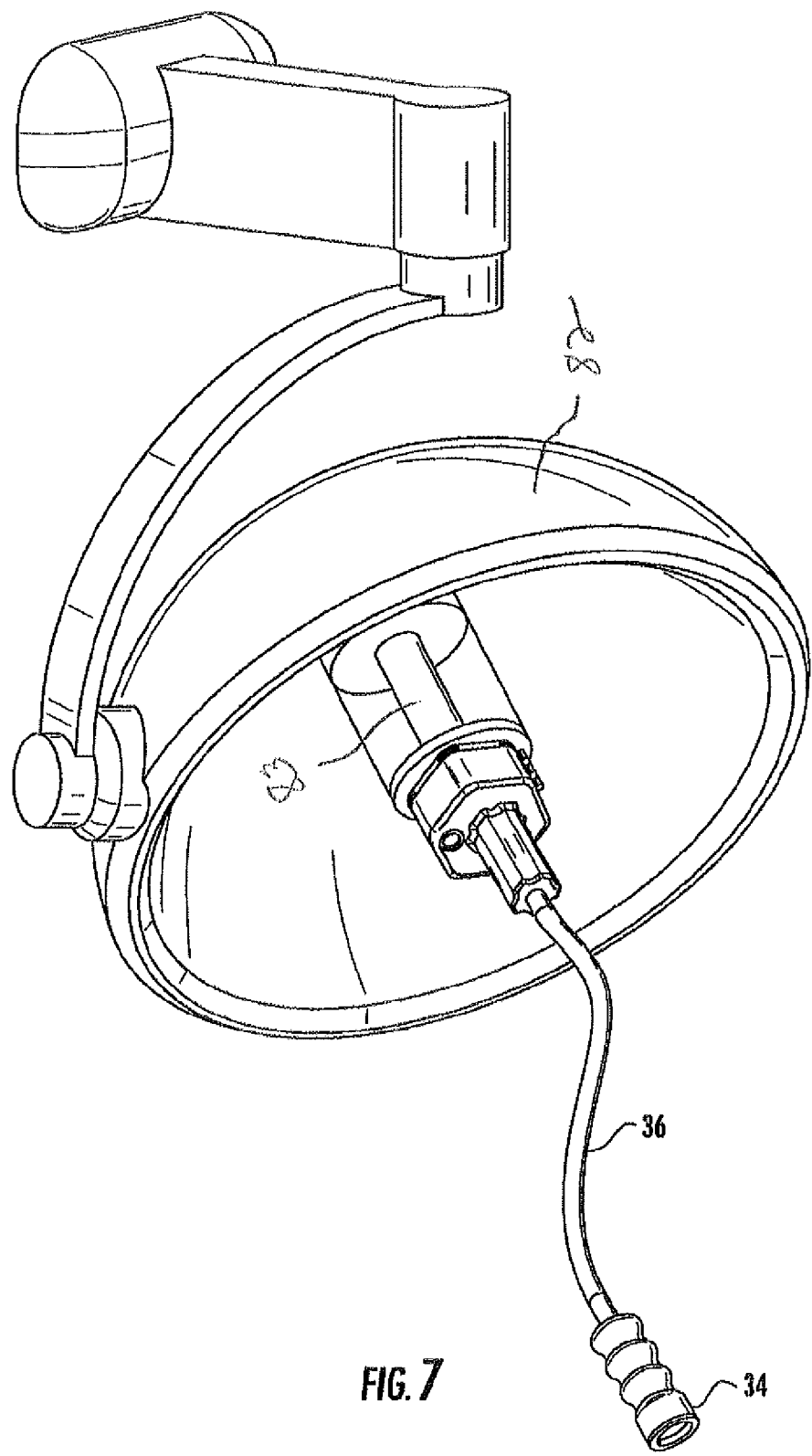
FIG. 7 is a front perspective view of the embodiment of the surgical light as shown in FIG. 6 attached to the overhead surgical light.

The surgical light device 30 is adapted to connect to an overhead light. As described above, overhead surgical or medical lights are provided with generally cylindrical handles for manually adjusting the direction of the light. As shown in FIGS. 6 and 7, the surgical light device 30 is configured to operatively connect to the handle 83 of the overhead surgical light 82 for adjustable, targeted surgical lighting. In one embodiment, the threaded flange 48 extending proximally from the cover 40 may be threaded onto the handle.

Figure 8:
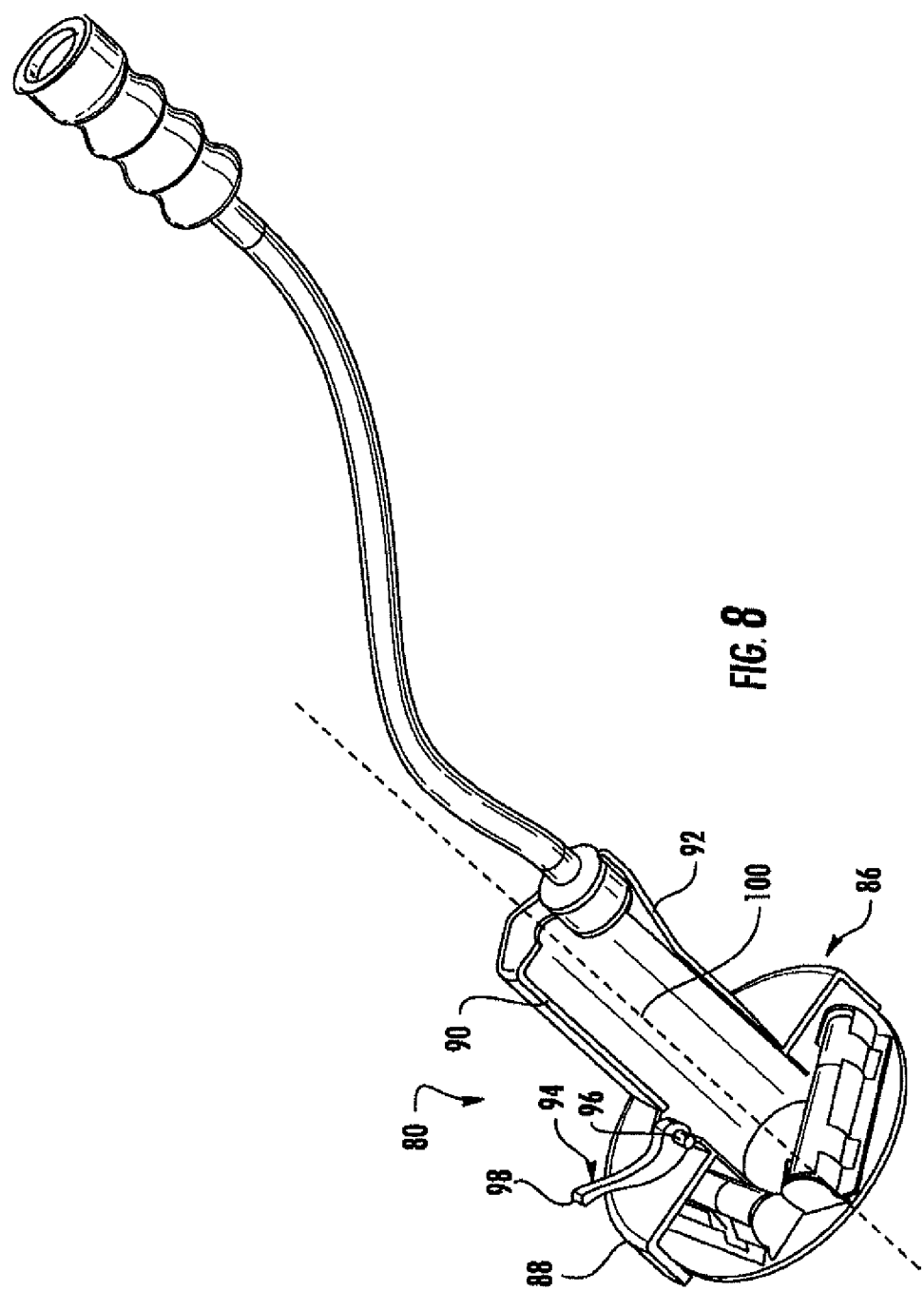
FIG. 8 is a partially cut-away longitudinal cross-section view of another embodiment of a flexible and adjustable surgical light for attachment to an overhead light comprising a camera.

In another embodiment, the cover 40 may define a central axial opening into the cavity 42 of the housing and the hollow projection 44 for slidingly receiving the handle 83 of the overhead light 82. The handle 83 slips into the cavity 42 defined by the housing 38 and within the bore defined by the axial projection 44 of the anchor member 32. An embodiment of a slide-on surgical light device is shown in FIG. 8 and generally designated at 80. The surgical light device 80 is suitable for use with an overhead surgical light including a camera integrated into the handle 83. The surgical light device 80 comprises an anchor member 86, including a housing 88 and a distal projection 90 defining a central longitudinal passage 92 therethrough. In this embodiment of the surgical light device 80, the flexible shaft 36 is affixed to the distal end of the projection 90 in a position offset from the opening of the passage 92. This configuration allows for a line-of-sight through the opening of the passage 92 for the camera, providing a surgical lighting system comprising the overhead camera operatively associated with flexible and adjustable surgical light device 80.

As shown in FIG. 8, the surgical light device 80 may further comprise a releasable locking mechanism 94. The locking mechanism 94 comprises a cam 96 and an integral lever 98 pivotally mounted on the projection 90 of the anchor member 32. The projection 90 defines an opening 100 into the passage 92 for receiving the cam 96. The lever 98 allows the user to manually pivot the cam 96 relative to the projection 90 to a locking position where the cam 96 extends into the passage 92 for frictionally securing the anchor member 86 to the handle 83 of the overhead surgical light 82. This arrangement is suitable for use with the overhead surgical light 82 and camera as well as other slide-on embodiments of the surgical light device 30, 80 for securely attaching the anchor member 32 to the overhead light. Ideally, the locking mechanism 94 is activated with one hand for positively engaging the handle 83 of the overhead surgical light 82. It is understood that the locking mechanism 94 is similarly easily released for removing the surgical light device 80.

Threaded or slide-on connection of the surgical light device 30, 80 to an overhead light provides a reliable and convenient means for mounting the surgical light device 30, 80 for use. It is understood that the surgical light device 30, 80 is not in any way limited to the connecting or mounting means described herein, but may alternately comprise any other suitable arrangement which enables connection of the surgical light device 30, 80 to the overhead light. For example, one skilled in the art should appreciate that the means of attaching the surgical light device 30, 80 described herein are exemplary and other means of attachment are possible, such as adhesive bonding, mechanical fastening, snap-fit coupling and the like.

In use, the surgical light device 30, 80 may be provided at inception of a surgery in a pre-sterilized condition within a sterile pouch (not shown). A member of the surgical team will open the sterile pouch to access the surgical light device 30, 80 and mount the anchor member 32 to the handle of the overhead surgical light (FIGS. 6 and 7). Once in position on the overhead light, the user may grasp the head portion 62 of the light assembly 34 or the flexible shaft 36 and manually direct the light assembly 34 at a target in the surgical field for illumination thereof. It is understood that the flexible shaft 36 then functions to maintain the position of the light assembly 34 by resisting movement of the shaft 36 from its selected shape. At the same time, the flexible shaft 36 is still selectively movable to illuminate another target in a second position as needed.

Figure 9:
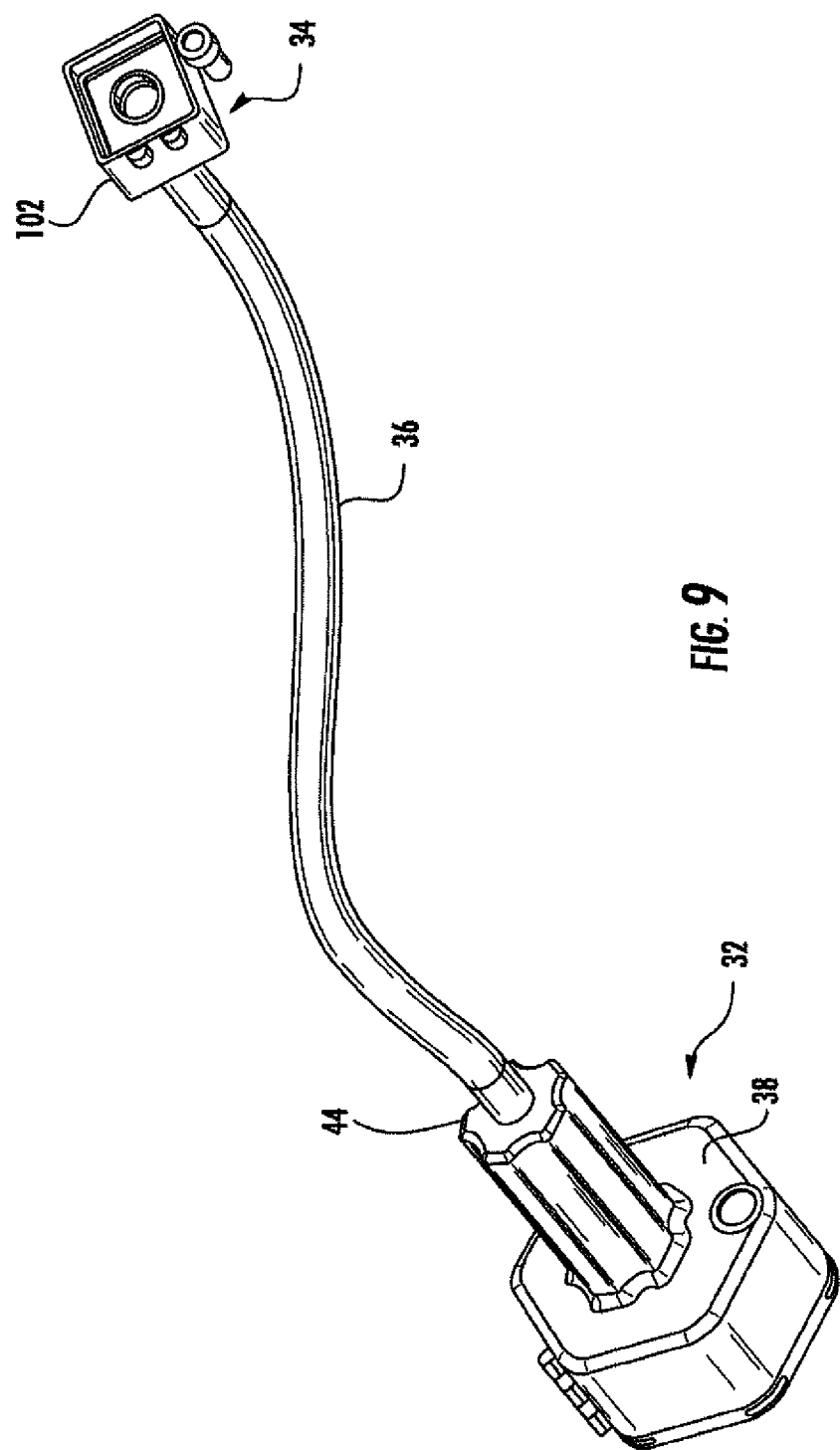
FIG. 9 is a perspective view of a third embodiment of a flexible and adjustable surgical light configured for attachment to an overhead light and showing a camera at a distal end of the surgical light.

The surgical light device 30, 80 may also serve as a platform for other functions. Referring to FIG. 9, a digital camera 102 is shown at the distal end of the shaft 36. In this embodiment, the surgical light device 30, 80 combines a light source 34 and adjacent camera 102 for capturing still or motion images. The camera 102 may be self-contained, including a lens and recording, processing and removable media storage capability, or the camera may allow for remote image transmission to a distant unit for processing, viewing and recording. In either application, the distal end of the shaft 36 provides an ideal location for the functional aspects of the camera 102 adjacent to the operative space, which further aids visualization of the work area. It is understood that a plurality of surgical light devices 30, 80 may be combined for the same effect, wherein a surgical light device may comprise the camera 102 and a second surgical light device 30, 80 anchored from the same or another overhead surgical light provides a light assembly 34.

In other embodiments of the surgical light device 30, 80 the distal end of the flexible shaft 36 may have other uses beyond lighting or image recording and transmission. For example, the light assembly 34 could be used as storage for delivery of an agent, such as a local topical antibiotic for local antisepsis. In this embodiment, the agent could be stored in the anchor member 32 and delivered at the distal end of the shaft 36, as needed, by the surgical team. It is understood that this use is merely exemplary of the utility of proximal storage in the anchor member 32 and delivery at the distal end of the shaft 36. Other opportunities using the surgical light device 30, 80 for storage and delivery in a surgical setting will be apparent to those of ordinary skill in the art.

Figure 10:
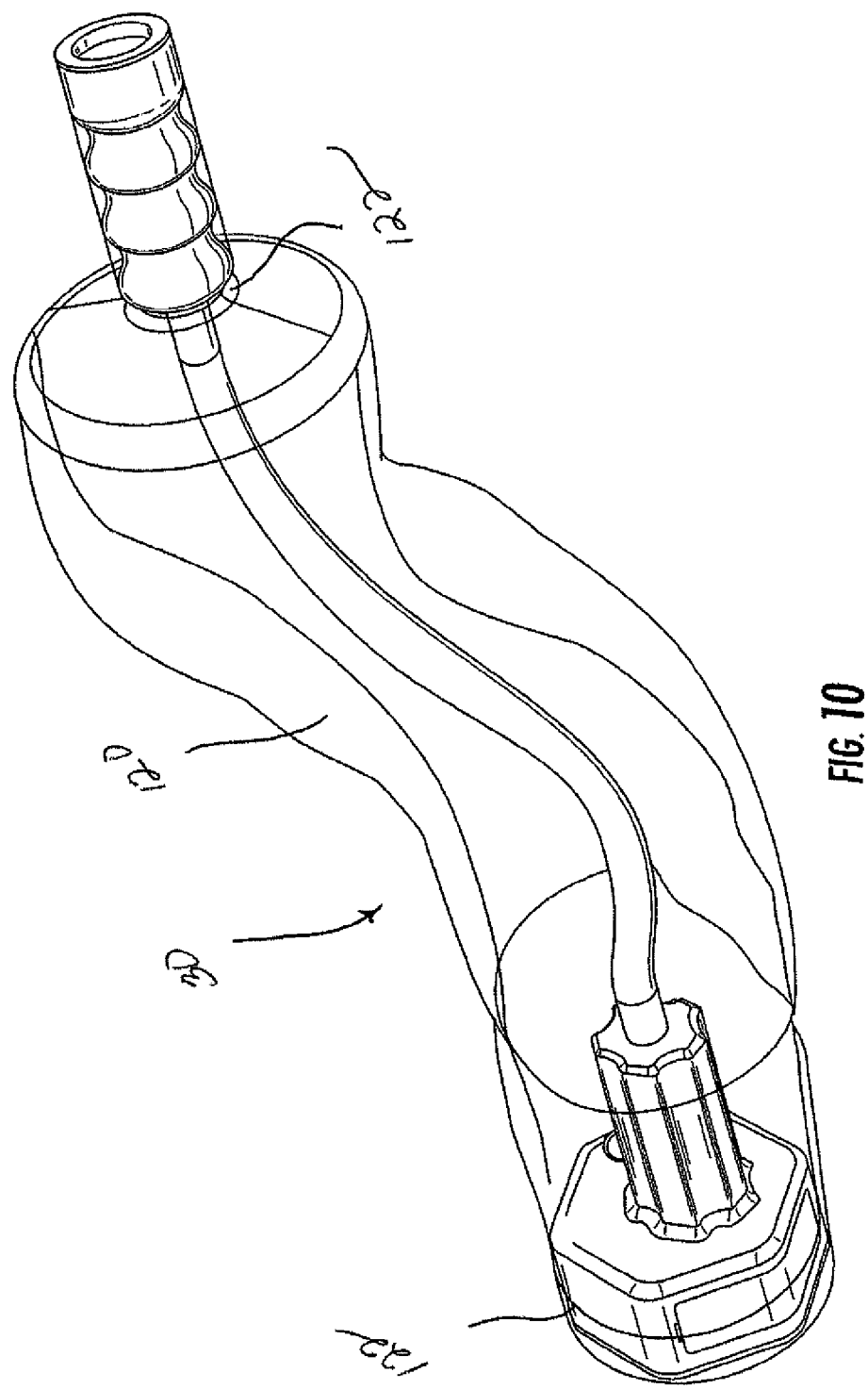
FIG. 10 is a perspective view of the embodiment of the surgical light as shown in FIG. 1 including a first embodiment of a sterile sleeve.
Figure 11:
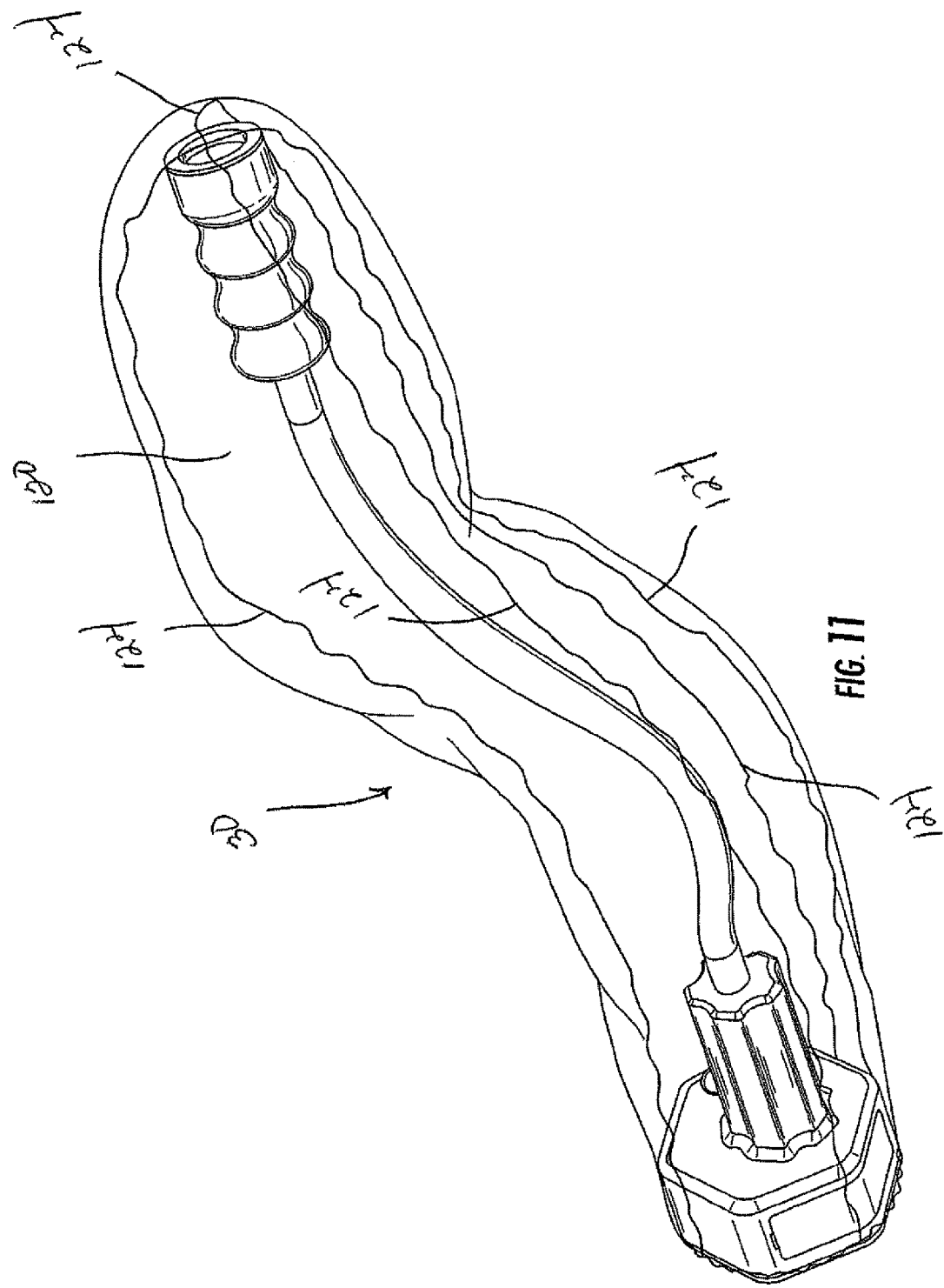
FIG. 11 is a perspective view of the embodiment of the surgical light as shown in FIG. 1 including a second embodiment of a sterile sleeve.
Figure 12:
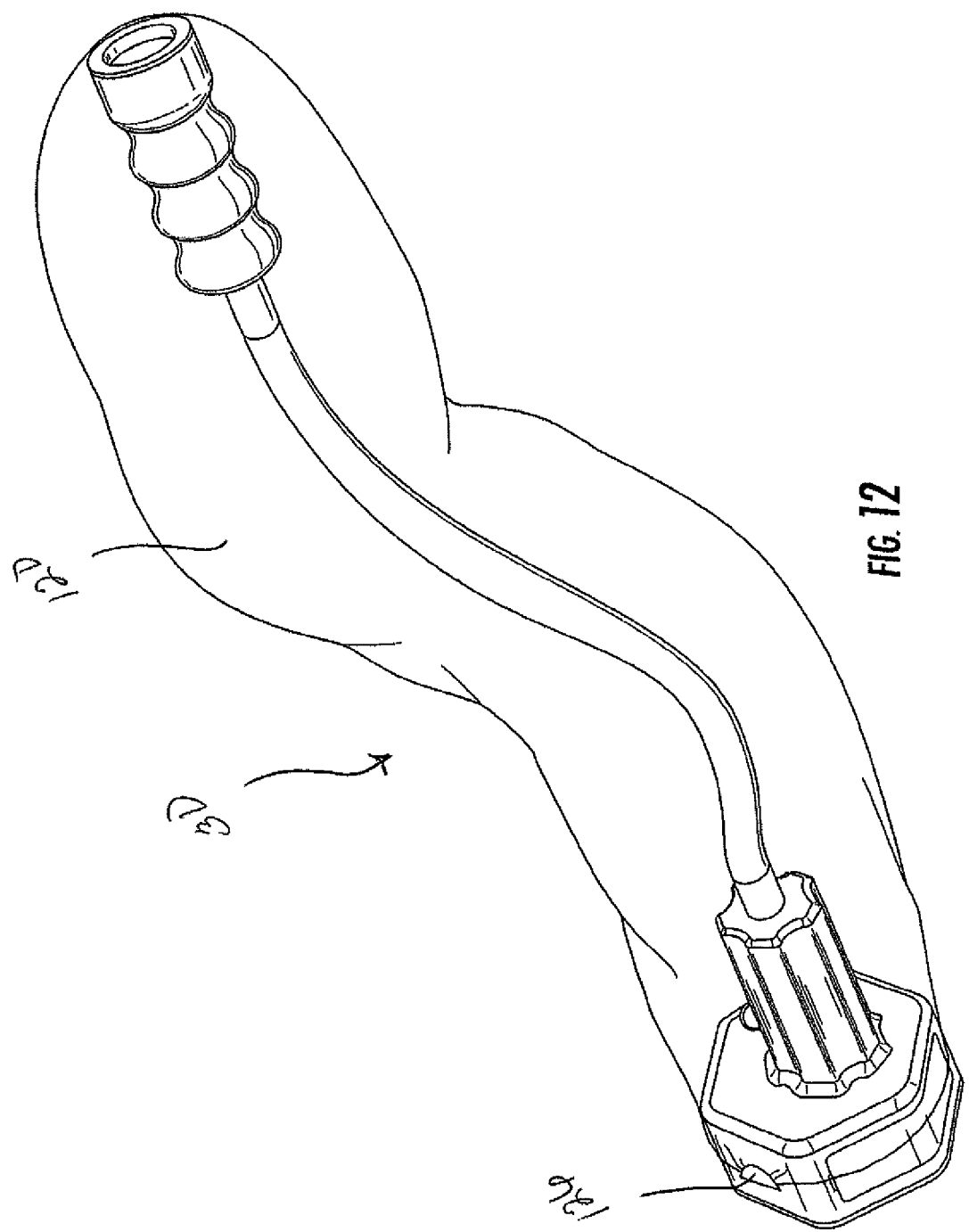
FIG. 12 is a perspective view of the embodiment of the surgical light as shown in FIG. 1 including a third embodiment of a sterile sleeve.
Figure 13:
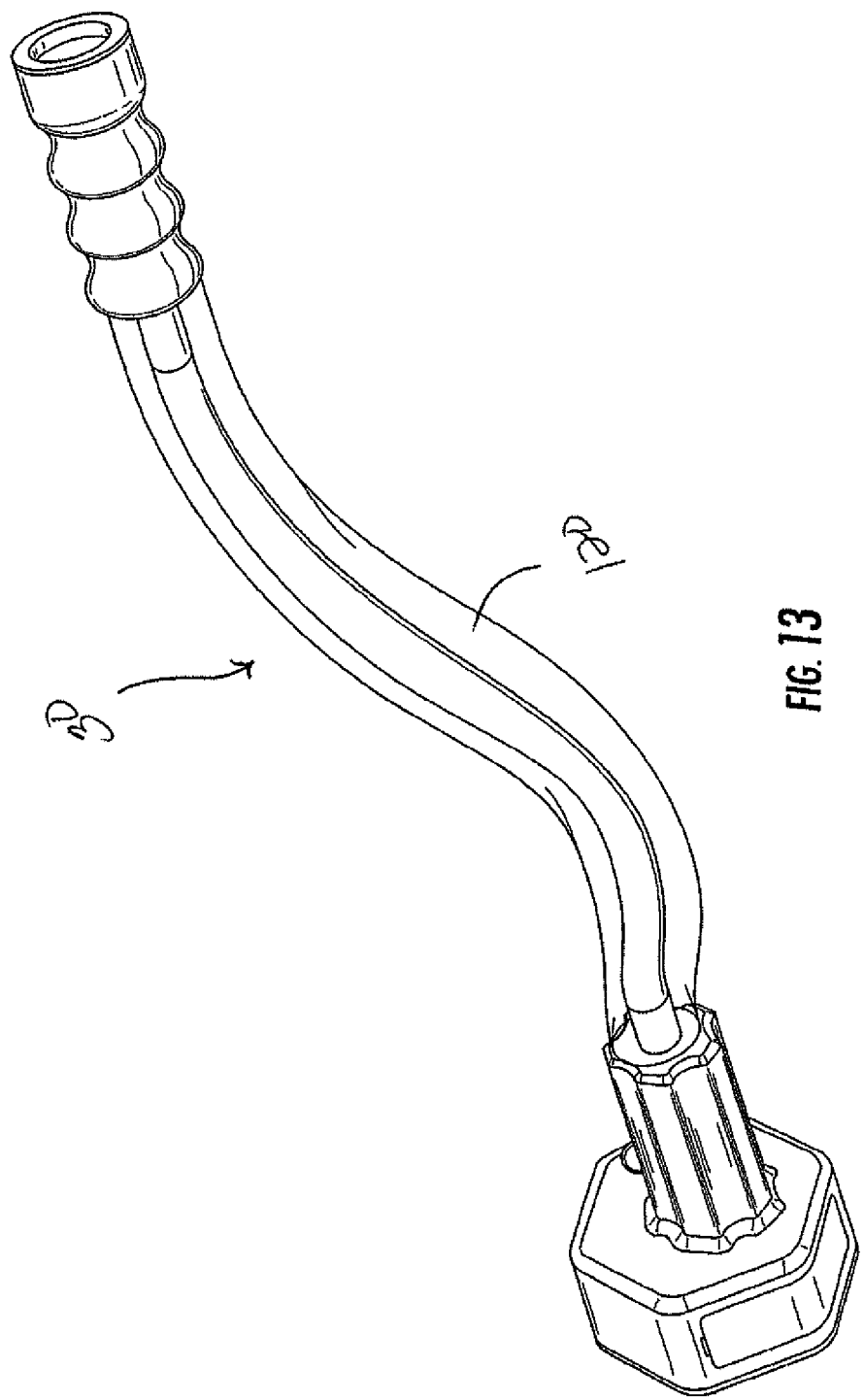
FIG. 13 is a perspective view of the embodiment of the surgical light as shown in FIG. 1 including a fourth embodiment of a sterile sleeve.

Referring now to FIGS. 10-13, a disposable sterile sleeve 120 may be provided for enclosing the surgical light device 30. The sterile sleeve 120 is a clear, plastic tubular element closed at one end for receiving the surgical light device 30, 80. In one embodiment, elastic bands 122 at a proximal end and a distal end secure the sleeve 120 to the surgical light device 30, 80 (FIG. 10). As shown in FIG. 11, a plurality of elastic cords 124 running the length of the sleeve 120 can be used for securely conforming the sterile sleeve 120 to the surgical light device 30, 80. Preferably, the elastic cords 124 do not obscure the light at the end of the light assembly 34. In another embodiment, a plurality of pinch holes 126 (only one of which is shown in FIG. 12) are provided in the anchor member 32 for holding the sterile sleeve 120 in place over the surgical light device 30, 80. In a further embodiment shown in FIG. 13, the sterile sleeve 120 can be a thermoformed or injection molded tube that fits snugly, or snaps into place, over the surgical light device 30, 80.

The surgical lighting device 30, 80 described herein has many advantages and is particularly useful for delivering targeted and adjustable light to a work area during a surgical procedure. The surgical light device 30, 80 utilizes existing overhead light systems for secure and adjustable anchorage provided by the handles on the overhead lighting. The flexibility of the shaft 34 allows the operating team to direct the light 36 into the surgical site at angles not achievable with an overhead surgical light or a head lamp. Moreover, the various orientations downward into the surgical working space achieved by the flexible shaft is effectively infinite. Applications for the adjustable light device 30, 80 are wide ranging, specifically to a wide range of medical procedures in the areas of surgery where incisions into the body require lighting for direct visualization of internal structures, including orthopedics, cardiovascular surgery, neurosurgery, oncology, plastic surgery and wide range of other surgical approaches. The surgical light device 30, 80 is especially well-suited for minimally invasive surgery, sometimes called minimal incision surgery. In these procedures, small incisions are used and the surgeon requires well targeted illumination to light the working space within the body.

Although the surgical light device and system has been shown and described in considerable detail with respect to only a few exemplary embodiments thereof, it should be understood by those skilled in the art that we do not intend to limit ourselves to the embodiments since various modifications, omissions and additions may be made to the disclosed embodiments without materially departing from the novel teachings and advantages, particularly in light of the foregoing teachings. For example, the surgical light device may be mounted to any suitable overhead structure, or to structure that is not overhead. Accordingly, we intend to cover all such modifications, omission, additions and equivalents as may be included within the spirit and scope of the surgical light device as defined by the following claims. In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures.

We claim:

1. An adjustable light for a medical environment including an overhead light having a light handle for manually adjusting the position of the overhead light, the light handle defining a longitudinal axis, the adjustable light comprising:
   a first housing defining a proximal surface, an opposite distal surface and an interior cavity therebetween, the housing further defining an opening to said interior cavity, said opening defined between said proximal surface and said distal surface;
   said distal surface including an elongated projection projecting distally therefrom, said elongated projection elongated along a central axis coincident with the longitudinal axis of the light handle when the first housing is coupled to the light handle, and said elongated projection sized and configured to be used as a handle for manually adjusting the orientation of the overhead light;
   a power supply sized to be received through said opening into said interior cavity of said first housing;
   a second housing including a lamp;
   an elongated flexible shaft connected at a proximal end of the elongated flexible shaft to said elongated projection of the first housing along said central axis of said elongated projection, and connected at a distal end of the elongated flexible shaft to the second housing, wherein the elongated flexible shaft is selectively movable along a length of said flexible shaft relative to the first housing to position said lamp relative to a target in the medical environment for illuminating the target; and electrical wiring extending from said first housing along said elongated flexible shaft to said lamp in said second housing and connectable to said power supply when the power supply is received into said interior cavity of said first housing, wherein said first housing is configured for releasably coupling to the light handle with said proximal surface adjacent the overhead light, wherein said opening is arranged on said housing to permit access to said interior cavity when said first housing is coupled to the light handle, wherein said elongated flexible shaft is hollow to receive said electrical wiring therethrough, wherein said elongated projection is hollow with an opening at a distal end thereof for communication with said elongated flexible shaft to receive said electrical wiring therethrough, and in communication with said interior cavity at a proximal end of the elongated projection; and wherein said elongated projection is configured to receive a portion of the light handle of the overhead light.

2. The adjustable light as recited in claim 1, wherein the lamp includes an LED.

3. The adjustable light as recited in claim 2, wherein the lamp further includes a PC board for controlling the LED, the PC board connected to the electrical wiring.

4. The adjustable light as recited in claim 1, wherein the lamp includes a light bulb, a lens, and a reflector.

5. The adjustable light as recited in claim 1, wherein the power supply includes batteries.

6. The adjustable light as recited in claim 1, wherein the power supply is a rechargeable electrical power source.

7. The adjustable light as recited in claim 1, wherein said elongated flexible shaft is configured to be manually deformed to a position in which the elongated flexible shaft remains until manually deformed.

8. The adjustable light as recited in claim 1, wherein said elongated projection includes a cam lock for engaging the portion of the light handle received therein for releasable coupling said first housing to the light handle of the overhead light.

9. The adjustable light as recited in claim 1, further comprising a protective sleeve disposed over said second housing, said elongated flexible shaft and at least a portion of said first housing.

10. A lighting system for a medical environment including a ceiling, the lighting system comprising:

an overhead light adapted to be suspended from the ceiling, the overhead light including a light handle for manually adjusting the position of the overhead light; and an adjustable light for mounting on the overhead light, the adjustable light comprising;

a first housing defining a proximal surface, an opposite distal surface and an interior cavity therebetween, the housing further defining an opening to said interior cavity, said opening defined between said proximal and said distal surface;

said distal surface including an elongated projection projecting distally therefrom, said elongated projection sized and configured to be used as a handle for manually adjusting the orientation of the overhead light;

a power supply sized to be received through said opening into said interior cavity of said first housing;

a second housing including a lamp;

an elongated flexible shaft connected at a proximal end of the elongated flexible shaft to said elongated projection of the first housing and at a distal end of the elongated flexible shaft to the second housing, wherein the elongated flexible shaft is selectively movable along a length of said flexible shaft relative to the first housing to position said lamp relative to a target in the medical environment for illuminating the target; and electrical wiring extending from said first housing along said elongated flexible shaft to said lamp in said second housing and connectable to said power supply when the power supply is received into said interior cavity of said first housing, wherein said first housing is configured for releasably coupling to the light handle with said proximal surface adjacent the overhead light, wherein said opening is arranged on said housing to permit access to said interior cavity when said first housing is coupled to the light handle, wherein said elongated flexible shaft is hollow to receive said electrical wiring therethrough, wherein said elongated projection is hollow with an opening at a distal end thereof for communication with said elongated flexible shaft to receive said electrical wiring therethrough, and in communication with said interior cavity at a proximal end of the elongated projection; and wherein said elongated projection is configured to receive a portion of the light handle of the overhead light.

11. The lighting system as recited in claim 10, wherein the lamp includes an LED.

12. The lighting system as recited in claim 11, wherein the lamp further includes a PC board for controlling the LED, the PC board connected to the electrical wiring.

13. The lighting system as recited in claim 10, wherein the power supply is a rechargeable electrical power source.

14. The lighting system as recited in claim 10, wherein said elongated flexible shaft is configured to be manually deformed to a position in which the elongated flexible shaft remains until manually deformed.

15. The adjustable light as recited in claim 10, wherein said elongated projection includes a cam lock for engaging the portion of the light handle received therein for releasable coupling said first housing to the light handle of the overhead light.

16. The adjustable light as recited in claim 10, further comprising a protective sleeve disposed over said second housing, said elongated flexible shaft and at least a portion of said first housing.

* * * * *